United States Patent
Anidjar et al.

[11] Patent Number: 6,036,723
[45] Date of Patent: Mar. 14, 2000

[54] SURGICALLY ANASTOMOSABLE TRANSCUTANEOUS VASCULAR PROTHESIS AND SET COMPRISING THE SAME

[75] Inventors: Samy Anidjar, Paris; Gérard Chevillon, Montrouge, both of France

[73] Assignee: B. Braun Celsa, France

[21] Appl. No.: 08/983,261

[22] PCT Filed: Apr. 24, 1997

[86] PCT No.: PCT/FR97/00734

§ 371 Date: Jun. 3, 1998

§ 102(e) Date: Jun. 3, 1998

[87] PCT Pub. No.: WO97/41804

PCT Pub. Date: Nov. 13, 1997

[30] Foreign Application Priority Data

May 2, 1996 [FR] France ................................. 96 05505
Apr. 8, 1997 [FR] France ................................. 97 04288

[51] Int. Cl.[7] .......................................... A61F 2/06
[52] U.S. Cl. .................................... 623/1; 623/12
[58] Field of Search .............................. 623/1, 12

[56] References Cited

U.S. PATENT DOCUMENTS

| | | |
|---|---|---|
| 3,986,828 | 10/1976 | Hoffman, Jr. et al. . |
| 4,562,596 | 1/1986 | Kornberg . |
| 5,078,726 | 1/1992 | Kreamer .................... 623/1 X |
| 5,122,154 | 6/1992 | Rhodes ...................... 606/198 |
| 5,123,917 | 6/1992 | Lee ............................... 623/1 |
| 5,195,984 | 3/1993 | Schatz . |
| 5,282,824 | 2/1994 | Gianturco . |
| 5,316,023 | 5/1994 | Palmaz et al. .......... 606/198 X |
| 5,366,473 | 11/1994 | Winston et al. ............ 606/198 |
| 5,383,928 | 1/1995 | Scott et al. .................. 673/1 |
| 5,489,295 | 2/1996 | Piplani et al. ............... 623/1 |
| 5,507,769 | 4/1996 | Marin et al. ............... 606/198 |
| 5,522,880 | 6/1996 | Barone et al. .......... 606/195 X |
| 5,522,883 | 6/1996 | Slater et al. ................. 623/1 |
| 5,562,724 | 10/1996 | Vorwerk et al. ....... 606/198 X |
| 5,562,725 | 10/1996 | Schmitt et al. .............. 623/1 |
| 5,575,818 | 11/1996 | Pinchuk ....................... 623/1 |
| 5,578,071 | 11/1996 | Parodi ......................... 623/1 |
| 5,591,229 | 1/1997 | Parodi ......................... 623/1 |
| 5,628,783 | 5/1997 | Quiachon et al. ....... 606/195 X |
| 5,639,278 | 6/1997 | Dereume et al. ........ 623/12 X |
| 5,669,924 | 9/1997 | Shaknovich ................ 623/1 |
| 5,683,451 | 11/1997 | Lenker et al. ............... 623/1 |
| 5,749,880 | 5/1998 | Banas et al. ................ 623/1 |
| 5,755,773 | 5/1998 | Evans et al. ................ 623/1 |
| 5,769,887 | 6/1998 | Brown et al. ............... 623/1 |
| 5,824,040 | 10/1998 | Cox et al. ................... 623/1 |
| 5,855,598 | 1/1999 | Pinchuk ....................... 623/1 |
| 5,934,286 | 8/1999 | Maginot ...................... 623/1 |

FOREIGN PATENT DOCUMENTS

| | | |
|---|---|---|
| 556850 | 8/1993 | European Pat. Off. . |
| 0684022 | 11/1995 | European Pat. Off. . |
| 8806026 | 8/1988 | WIPO . |
| 9521592 | 8/1995 | WIPO . |

*Primary Examiner*—David H. Willse
*Assistant Examiner*—Suzette J. Jackson
*Attorney, Agent, or Firm*—Rothwell, Figg, Ernst & Kurz, p.c.

[57] ABSTRACT

A vascular prosthesis to be implanted by the percutaneous endoluminal route is provided according to an embodiment of the invention. The vascular prosthesis includes a flexible sleeve to channel blood therein, and a tubular armature (or stent) to which the sleeve is connected essentially coaxially, the armature being capable of having a first diameter or a second diameter larger than the first, so that the prosthesis is in the form of a single tube or bifurcated tube assuming a radially constricted state for its percutaneous vascular implantation, or a radially opened out state, once it is vascularly implanted, additionally including a vascularly anastomosable terminal portion of sleeve which extends, or is added onto, the flexible sleeve, beyond the armature, this portion being therefore suitable to be anastomosed, in particular by suture, to at least one vessel or vessel substitute.

21 Claims, 9 Drawing Sheets

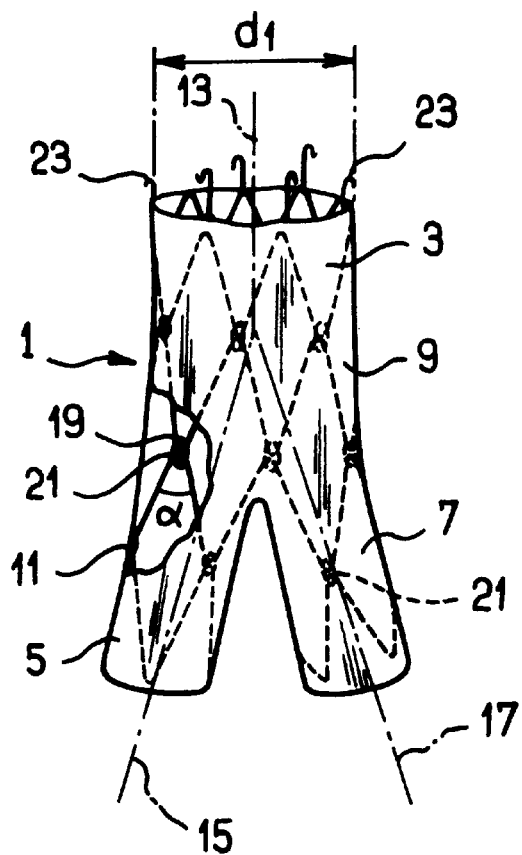
FIG_1
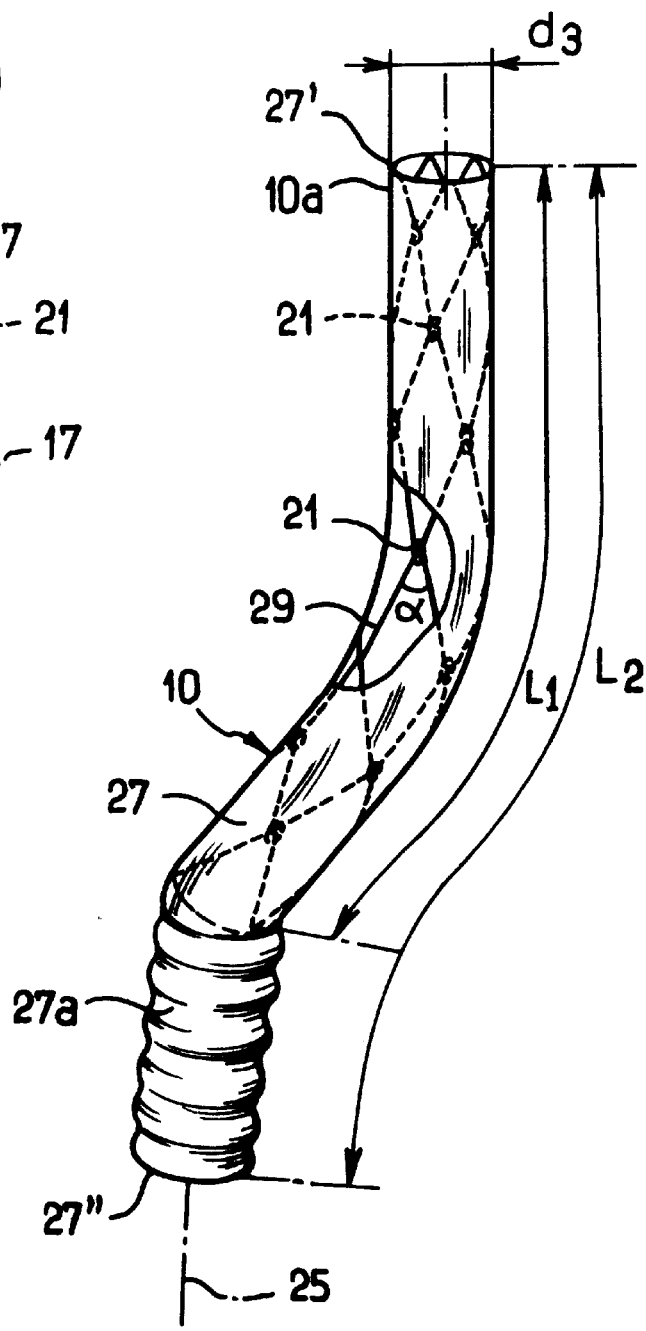
FIG_2

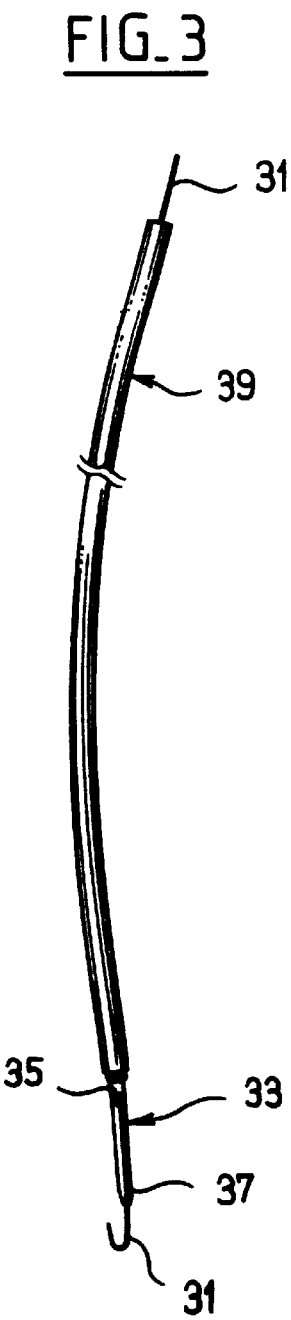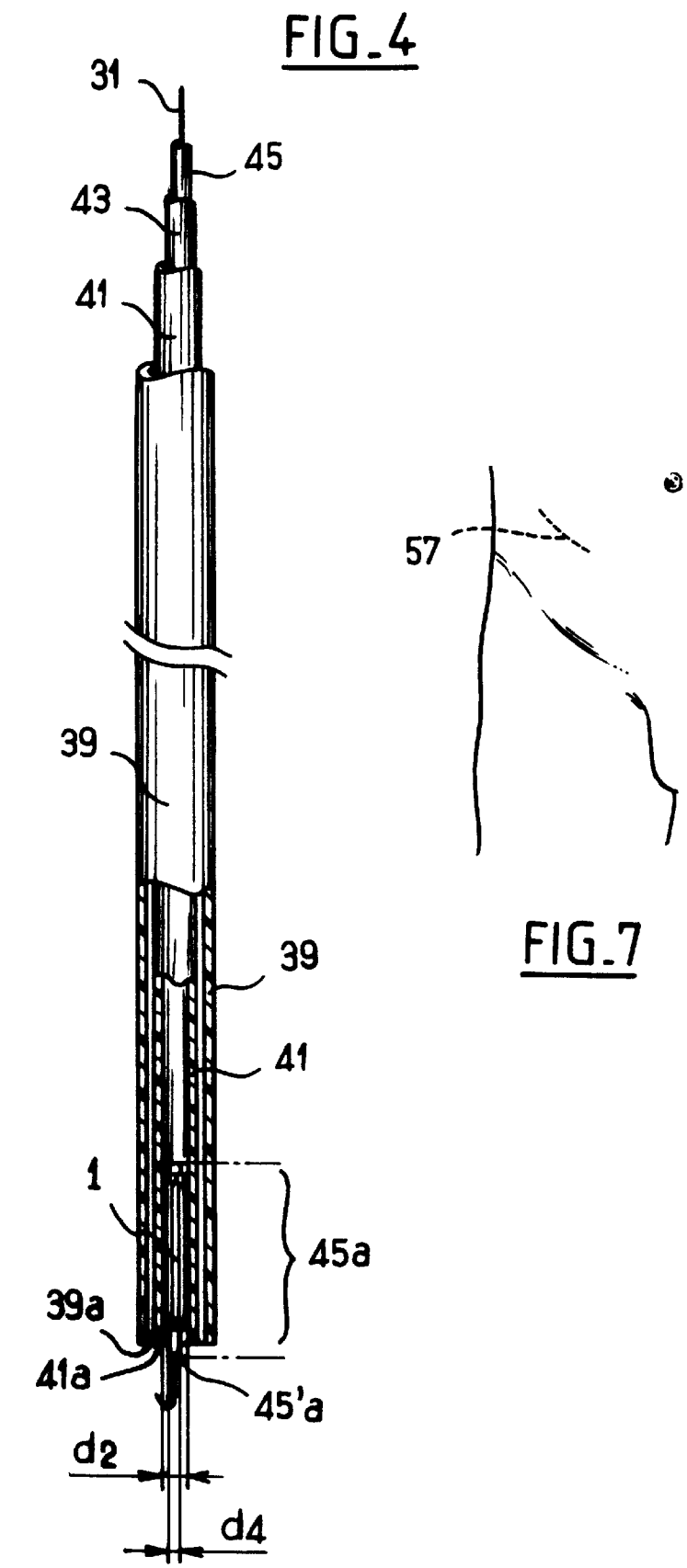

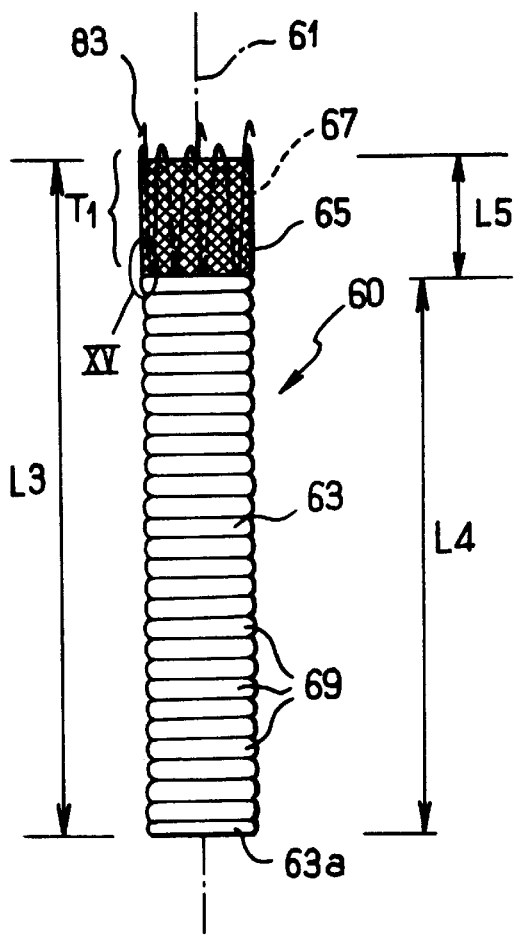
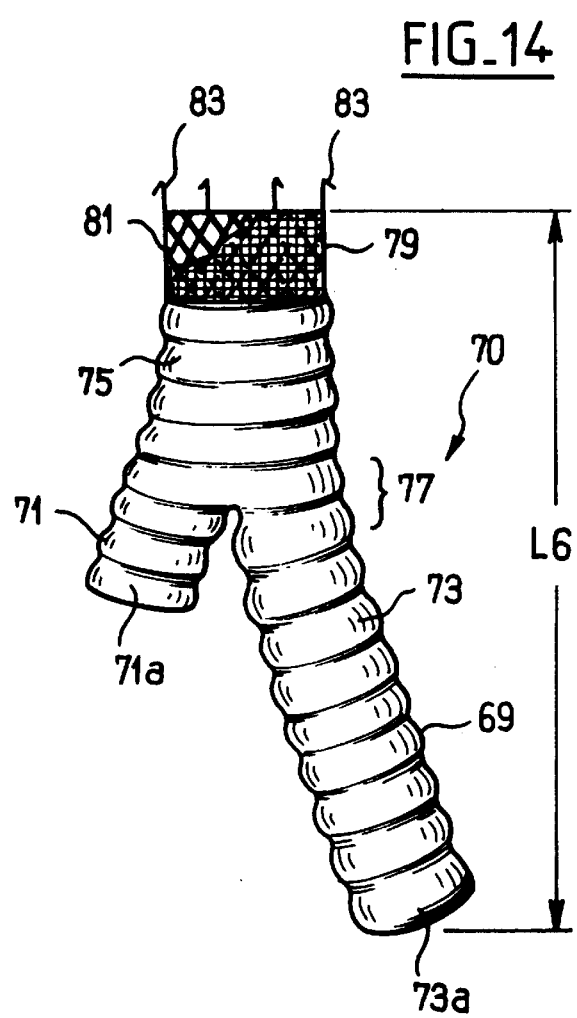
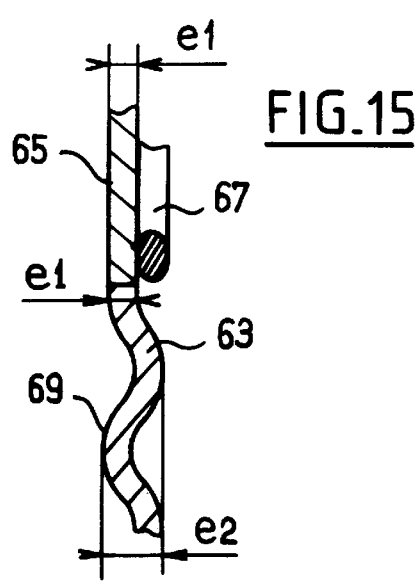

SURGICALLY ANASTOMOSABLE TRANSCUTANEOUS VASCULAR PROTHESIS AND SET COMPRISING THE SAME

BACKGROUND OF THE INVENTION

The object of the invention is to improve the current conditions of "treatment" of damaged areas of certain anatomical channels or ducts.

It relates, in particular, to improving the blood circulation conditions in a damaged vascular zone, most particularly if the vessel(s) has(have) one or more aneurysms.

More particularly, it relates to improving the current conditions of treatment of aneurysms overlapping various vessels in communication therebetween, especially aortic aneurysms overlapping one or more iliac vessels, and even the hypogastric arteria.

At present, it is known to use intraluminal tubular prostheses implantable through a percutaneous intraluminal access (Seldinger approach, especially) to mitigate degeneration of or damage to anatomical channels.

These endoscopic prostheses (or endoprostheses), the object of which is to form a substitute for the duct, at least locally, frequently comprise:

a substantially non-"self-supporting" sleeve or sheath, and a tubular armature (or stent) essentially coaxial with the sheath, the armature being arranged to be radially constricted or opened out.

The armature then serves as a support for the sleeve (which therefore customarily has no intrinsic "strength" and collapses if it is not supported) and permits the percutaneous endoluminal implantation of the prosthesis, the sleeve adapting to the shape of its armature, especially to form a tube making it possible to channel a body fluid, when the armature is opened out radially.

Examples of prostheses of this type which form, locally, a substitute for the channel, are described in particular in U.S. Pat. No. 5,282,824. In WO-A-95/21592, it is even provided to attach, to a bifurcated prosthesis of this type, a tubular extension prosthesis, facilitating the positioning of the bifurcated prosthesis, thus permitting the two secondary branches thereof, which originate from the bifurcation, to be short, whilst still permitting the length of the extension to be adapted as required.

But these vascular implants introduced by the percutaneous endoluminal route may be contra-indicated in certain clinical cases, more particularly when the aneurism(s) is/are too extensive and, starting from the aorta, spread over several vessels, beyond the iliac bifurcation (outer and/or inner iliacs), and even extend as far as the hypogastric artery.

A solution may then consist in surgically implanting a vascular prosthesis for local substitution of the vessel, of the "bridging" type. But this involves "heavy" surgical intervention, in order to expose all the damaged vascular region(s), in general with thoracic and/or abdominal stripping. Such a prosthesis is described for example in WO-A-8806026 or U.S. Pat. No. 3,986,828.

However, the invention aims precisely to avoid that, thus embracing the reasons which led to the adoption of percutaneous endoluminal implants.

SUMMARY OF THE INVENTION

In order to satisfy these contradictory requirements, the invention proposes a vascular prosthesis arranged to be implanted by the percutaneous endoluminal route. The vascular prosthesis includes a flexible sleeve (or sheath) for channelling blood therein, and a tubular stent (or armature) (to which the sleeve is customarily connected), the stent being capable of having a first diameter or a second diameter larger than the first, so that the prosthesis is in the form of a single or bifurcated tube assuming a radially constricted, closed state, for its vascular implantation, or a radially opened out, open state, once it is vascularly implanted, the prosthesis additionally comprising a vascularly anastomosable terminal portion of sleeve which extends, or is added onto, one end of the said flexible sleeve, this terminal portion therefore being arranged to be anastomosed, in particular by suture, to at least one vessel or vessel substitute.

It is thus possible to perform a surgical connecting operation (in particular by suturing) between this tube and, for example, an anatomical channel (such as a vessel) or, if this channel is too damaged at the place where the extension of the sheath of the prosthesis has been positioned, a substitute for the channel.

And by associating with a "reduced" surgical procedure an endoluminal treatment by fitting a prosthesis or prostheses, the range of use of these implants will be widened.

In the case where the vascular ailment concerns one or more "complicated" aneurisms, a characteristic of the invention relates to the specific use of such a prosthesis (that can be implanted by the percutaneous endoluminal route) for the treatment of such a spread of an aneurism over several branched vessels communicating with one another, this treatment being effected, once the prosthesis is implanted, by vascular surgery (with anastomosis) between the vascularly anastomosable terminal percutaneous portion of sleeve which therefore extends (or is added onto) the said flexible sleeve of the prosthesis and the vessel or substitute of vessel.

For an aneurismal treatment, the prosthesis of the invention will advantageously be a prosthetic branch of a bifurcated prosthesis comprising, in order to channel the blood, a principal tubular section connected to secondary tubular sections, at least one of which will be arranged to be provided with the said prosthetic branch with free end portion devoid of supporting armature (anastomosable portion).

According to another aspect, the invention moreover seeks to define the conditions of production of the sleeve (which may be in one or more parts) of one of the prostheses defined above.

The solution proposed advantageously consists in that the part of the sleeve located essentially facing the stent is radially extensible and/or assumes its radially open tubular form only under the action of this stent which serves as an armature for it (by supporting it) and which then has its second diameter, and the anastomosable terminal portion of sleeve is less radially extensible than the other portion and/or naturally assumes by itself a radially open tubular form.

In addition, the constituent materials or textures and/or the thicknesses of the said sleeve parts, respectively facing the armature and anastomosable, will preferably be different.

Of these characteristics, the thickness and the mechanical strength (self-supporting capability) are certainly the most important.

In fact, it is reasonable to consider that the above-mentioned self-supporting capability of the anastomosable terminal portion allows it to assume naturally (without any mechanical constraint) a radially open form (substantially circular in particular), to be (essentially) impermeable to the body fluid in question (blood; this being at least indirectly linked to the thickness), its relative "intrinsic" rigidity additionally allowing the practitioner to carry out anastomoses more easily. If nowadays the thickness and/or the material or texture of the other part of the sleeve located essentially facing the armature were to become, on the other hand, comparable to that of the said anastomosable section, then difficulties might arise when introducing and/or placing the implant in position by the transcutaneous endoluminal route.

This is why it appears preferable in the invention that the sleeve part which is to be opened out radially by the armature should have a lesser thickness than the anastomosable terminal portion which opens out by itself (if it has been previously deformed by radial constriction).

There only remains that the constituent materials or textures of each of the sleeve parts can play their part, for example by improving leaktightness, with respect to the blood, of the sleeve part which is to be opened out by the armature, or by permitting that same sleeve portion to be rendered radially extensible (resiliently or otherwise), while on the other hand, if necessary, keeping the anastomosable terminal portion essentially not radially extensible.

With regard to these characteristics of extensibility and radial non-deformability (a priori in compression) without appreciable effort, an important criterion is the possible use of sleeves already marketed respectively for endoluminal "transcutaneous" vascular implants and for "surgical" vascular implants, of the "bridging" implant type, the connection end to end of these two types of sleeves and their respective use already proved making it possible both to increase their reliability and to reduce the manufacturing cost.

Thus, it will be possible to combine the advantages of percutaneous endolumiial vascular implants with those of vascular substitution surgical implants.

Concerning the "thicknesses" of sleeve to which reference was made above, it will be noted that these are total thicknesses, including any possible thickness of embossing, corrugation, or created by any other "crease-preventing" means.

It should also be noted that the invention seeks to define the proportions which should advantageously be attributed to the said "anastomosable terminal portion" in relation to the total length of the sleeve of the implant between two opposed axial ends of the latter.

At first, it appeared preferable to limit this length of "terminal portion" to a marginal end region (see, for example, FIGS. 2 or 6 hereinafter).

In particular, it was first assumed that the implantation of the whole of the prosthesis by the percutaneous endoluminal route would require that at least the greater part of the axial length of the prosthesis be produced in the form of a "traditional endoluminal prosthesis", that is to say, with an armature of the aforesaid type supporting a sleeve substantially without intrinsic mechanical strength (fabric or equivalent which is scarcely rigid at all).

However, it has surprisingly proved that it may be preferable for it to be the other portion of the sleeve, previously termed "anastomosable terminal portion", which takes up the greater part of the length of this sleeve, just as is illustrated in FIGS. 13 and 14 hereinafter.

Thus, from one end therefore and over the greater part of its length, the sleeve will not advantageously be supported by any stent or armature for radial opening out (in the manner of transcutaneous implants), whether it is a stent which is self-expanding in zigzags or a stent that can be opened out by an internal inflation means, such as an inflatable balloon (as in U.S. Pat. No. 5,195,984, for example).

And if, like the current surgical vascular sleeves, this portion has a deformation capacity along the axis of the sleeve, it will he possible to benefit from considerable elongation favourable to anastomosis, the vascular fixing of the prosthesis to the vessel being itself ensured at the other end by means of hooks or equivalents typically borne by the armature or stent.

In relation to the foregoing, it will be noted that in particular, when it is a question of a bifurcated prosthesis (inverted "Y"-shape), the anastomosable sleeve portion will very advantageously extend from the end of at least one of the secondary sections (which is also a free end of the prosthesis), to beyond the region of bifurcation of the sections (see FIG. 14 hereinafter).

Still concerning the question of the length ratio between the anastomosable sleeve part and the part supported by the stent or armature, it will also be noted that, in practice, the axial length of this stent or armature will advantageously be just sufficient to provide radial opening of the sleeve portion which the armature or stent supports, the said supported sleeve portion itself advantageously having just the right length to ensure the necessary leaktightness with respect to the wall of the duct in question, in order to avoid appreciable leaks between the free end of this sleeve portion and the wall of the duct with which this sleeve portion is to come into contact, under the thrust of its supporting armature.

In other words, the length of the stent or armature and of the said corresponding portion of supported sleeve will advantageously be reduced to the minimum, in order to reserve all the rest of the length for the anastomosable surgical type of sleeve, thus optimising the structural characteristics of the two sleeve parts having regard to their function, with good guarantees as to the opening of the portion of the prosthesis "with stent" and a good leaktight contact at this location, while obtaining conditions favourable to anastomosis, at the opposed free end, and automatic leaktightness over the greater part of the length of the implant (without requiring additional treatment of the sleeve).

Another problem which the invention seeks to solve concerns the leaktightness with respect to the blood between the anastomosable terminal portion of the sleeve and the (cut) blood vessel through which this portion will have been engaged.

In fact, in order to ensure anastomosis between this terminal portion and the vessel (or substitute) in question, downstream of the aneurism, it was necessary for the vessel to be sectioned there. For the downstream part, anastomosis provides appropriate leaktightness between this vessel (or substitute) and the prosthesis. There remains the problem of the upstream part which receives the blood flow.

The solution proposed in the invention consists in adding to the prosthesis an annular means, such as a (leaktight) support ring to be arranged round the anastomosable terminal portion of sleeve in order to obtain both leaktightness with respect to the blood between the said annular means and this terminal section, and a leaktight fixing means in order thus to fix, round this support means, the cut vessel section through which this anastomosable terminal portion is passed.

The fixing means may be a tie which the practitioner will therefore tighten round the upstream part of the vessel in question, thus pressing this part against the support "ring". In order to provide leaktightness with respect to the blood between the "ring" and the terminal portion of sleeve, the former may be engaged very tightly round the latter and/or a complementary added-on sealing means may be provided, such as a plug of foam or fabric to be placed beneath the "ring", or a flexible flap of a fine material impermeable to the blood, fixed round the portion in question of the sleeve (away from its free end to be anastomosed) and folded over the "ring".

It should also be noted that in relation to the foregoing, the invention also concerns an assembly comprising the implant already described and the equipment for its implantation by the endoluminal transcutaneous route, as indicated in the accompanying claims 12 to 15.

A more detailed description will now be given below of the invention, both in its structural constitution and within the framework of its method of implementation.

BRIEF DESCRIPTION OF THE DRAWINGS

In the drawings which accompany this description:

FIG. 1 shows a bifurcated prosthesis for an aneurysm;

FIG. 2 shows a tubular prosthesis according to the invention, and intended, in this case, to serve as an extension of one of the sections of the prosthesis shown in FIG. 1;

FIG. 3 shows, on a small scale, a conventional guide thread engaged in the inside of a dilater of the percutaneous access route, which dilater itself slides in an implantation sheath;

FIG. 4 shows, on a larger scale, an implantation device which may be used for the positioning of one and/or other of the prostheses shown in FIGS. 1 and 2;

FIG. 7 shows, schematically, the area of the surgical intervention which is shown more precisely in FIG. 8, FIGS. 13 and 14 show, in front view, two alternative embodiments of the implant (single tube, FIG. 13; "Y"-shaped tube, FIG. 14), and FIG. 15 is a detail view in section according to XV in FIG. 13.

DETAILED DESCRIPTION OF THE PREFERRED EMBODIMENTS

With reference to these Figures only the application of the invention to the treatment of primary iliac aneurysms overlapping the hypogastric and external iliac arteries will be described hereinbelow, even though it could possibly be envisaged to apply the invention to channels other than vessels, or at least to other vascular conditions.

Figure 5:
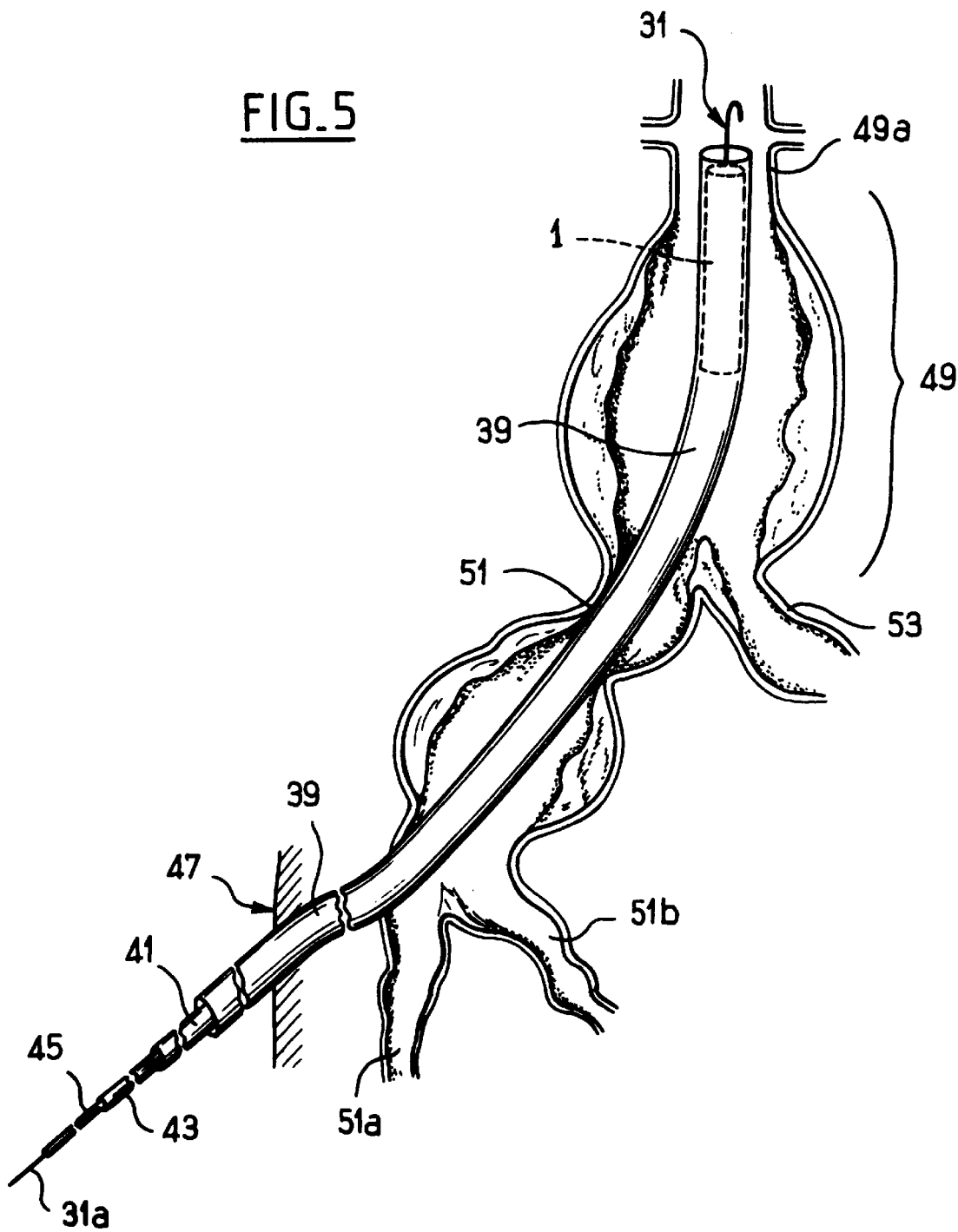
FIG. 5 shows, schematically, a method for positioning, via the percutaneous route, the bifurcated prosthesis shown in FIG. 1.
Figure 6:
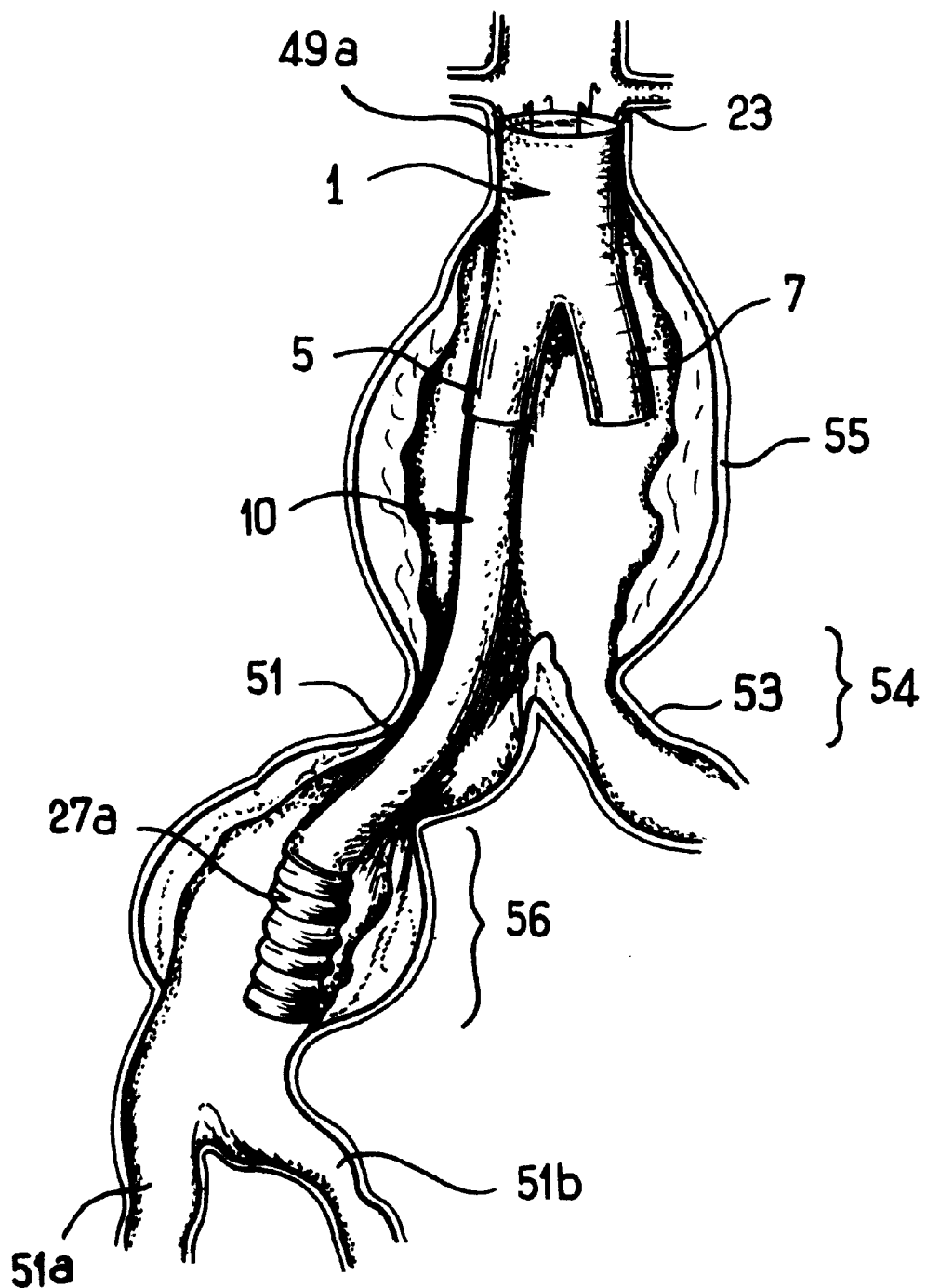
FIG. 6 shows the two prostheses shown in FIGS. 1 and 2 in place in the vessels which accommodate them.
Figure 8:
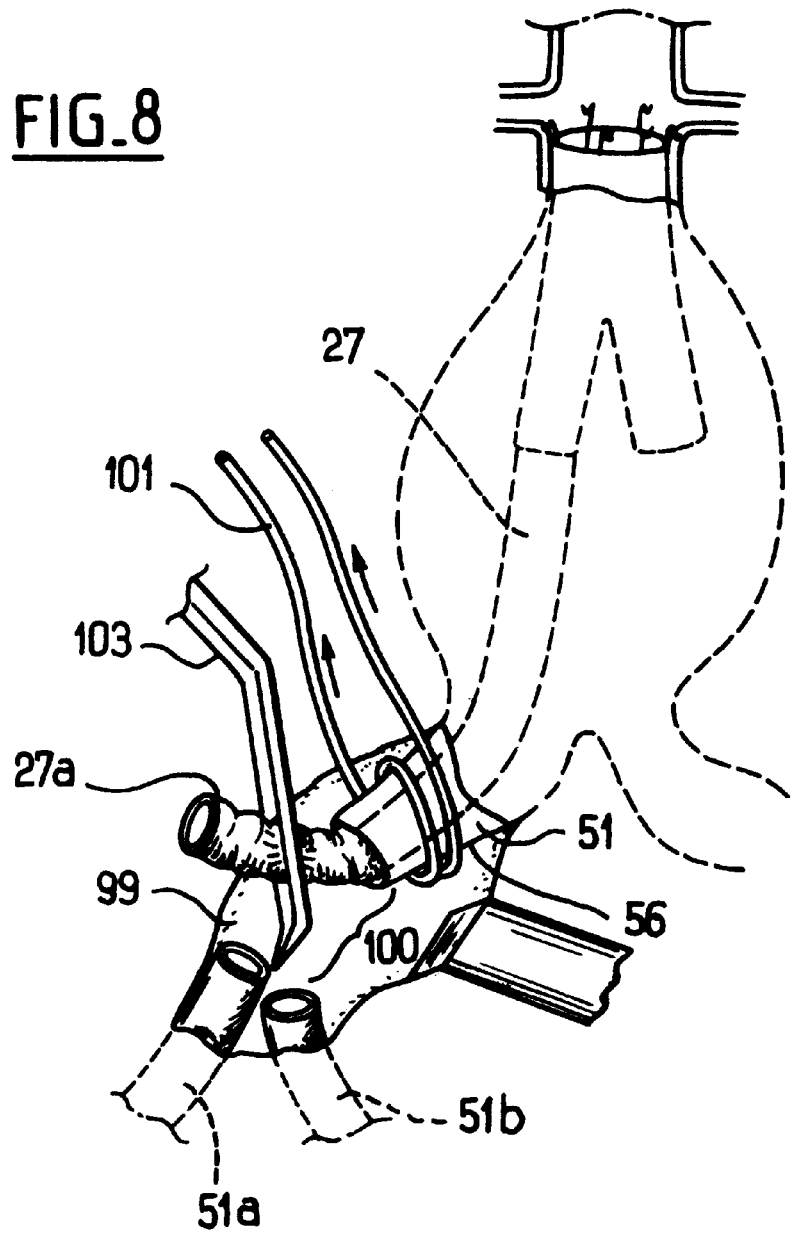
FIG. 8 shows a stage of surgical intervention where the practitioner recovers the anastomosable branch of the implant, after having carried out the necessary sectioning.

It should also be noted that FIGS. 5 and 6 show the inside of the body of the patient (in section), while FIGS. 8, and 10 to 12 show (except for the upper part of FIGS. 8 and 12), by solid lines, the region exposed for surgical intervention (at 99) and, by dotted lines, the location of the implant and the aortic aneurism.

FIG. 1, therefore, firstly shows diagrammatically a bifurcated vascular prosthesis 1.

The prosthesis 1 comprises a principal tubular section 3 dividing into two tubular branches 5, 7, both of shorter axial length than that of the section 3.

In order to constitute this form, the prosthesis consists of an outer sleeve of a flexible material 9 with practically no intrinsic mechanical strength, forming a "Y"-shaped tube assuming a trouser-like shape when the sleeve is reinforced or supported by an armature 11 to which it is fixed.

The framework 11 shown schematically comprises one or several metallic threads (such as of stainless steel) of some tenths of millimeters (for example of the order of 0.1 mm to 0.5 mm) in diameter, in a zigzag wound in a helix, the principal section 3 having the main axis 13, separating into two helixes having the axes 15 and 17 respectively, the secondary sections 5, 7 having diameters which are slightly less than that of the helix of the section 3.

Advantageously, for a good cohesion of the framework assembly 11, the apices (or zones of curvature) 19 of the zigzags of two adjacent winding turns are connected to one another by fasteners 21 which may consist of little rings, of buckles bound into the suture thread, or even of welding points.

For further detail relating to the embodiment of the framework 11, reference may be made, if necessary, to WO-A-95/21592.

It would also be possible to use one or more tubular stents constituted by a plurality of zigzag metal wires.

The armature 11 may extend only over part of the length of the implant 1.

In order to ensure its fixing to the vessel and a mechanical connection to the anastomosable implant 10 (region 27, FIG. 2) or 60 (stent 81, FIG. 13), the implant 1 will have a tubular or annular stent at least towards each of its opposed axial ends identified by the regions 11a (proximal end) and 11b, 11c (distal end).

It should be noted that, whatever version is used for the framework, the construction thereof ensures a resistance to crushing along the general axis 13 and the branching axes 15 and 17. It should likewise be noted that the prosthesis as presently illustrated is radially "auto-expandable", ie. that the rectilinear sections of the zigzag of the framework threads thereof have a tendency to extend laterally away from one another at an angle α which may be between approximately 20 and approximately 50° (diameter $d_1$; FIG. 1).

Such a prosthesis may, of course, furthermore be radially compressed to be introduced via the percutaneous route via a sheath or catheter of small diameter, this "radially narrowed" state being produced by a substantially parallel arrangement of the rectilinear sections of the threads of the zigzag of the framework (diameter $d_2$; FIG. 4). The segment of sleeve fixed to those thread will follow the narrowing or the radial expansion of the framework.

It should furthermore be noted that means (such as hooks) 23 for securing the prosthesis to the channel in question are preferably also provided. In FIG. 1, the hooks 23 are welded to threads of the zigzag situated at the free end of the principal section 3, the free end of the legs 5, 7 not having them.

FIG. 2 relates to a prosthesis 10 defining a single tube with a main axis 25.

The prosthesis 10 comprises, like the prosthesis 1, a tubular coating sleeve of woven material (or equivalent) 27, supported at the interior by a coaxial framework 29.

The framework 29 may reassume the filamentary structure of zigzags wound into a helix of the framework 111 is at the part where it opens out into only one tube (as on the sections 3, 5 or 7). The ties 21 are likewise shown in FIG. 2.

However, the particular feature of the prosthesis 10 consists most particularly in that the tubular framework 29 thereof only extends over an axial length $L_1$ which is less than the total length $L_2$ of the tubular sleeve 27 which surrounds it.

Thus, from its proximal end 27', the sleeve 27 is only supported (for example at its interior) by the framework 29 over only the length $L_1$ thereof, the end part (which extends from 27a to the distal end 27") being without one. If necessary, the end part 27a may be connected to a principal section of the covering, the length of which is $L_1$.

From the above, it will be understood that, like the prosthesis 1, the prosthesis 10 may be radially auto-expandable (diameter $d_3$ in the inactive position; FIG. 2) by the action of its framework 29, the section 27a of the covering adapting to the state of the prosthesis over the remainder of its length.

Even though it is possible to envisage using the prosthesis 10 by itself, this prosthesis 10 is in the example of the application given hereinbelow, an "extension prosthesis" of one of the legs 5, 7 of the bifurcated prosthesis.

FIGS. 3 to 5 show the means used to implant the prosthesis 1 and/or the prosthesis 10 by the percutaneous route.

FIG. 3 shows one part of the implanting equipment comprising a fine metallic guide 31 with a curved distal end, onto which an introducing means 33 with a radio-opaque mark 35 and with a pointed end 37 has been slid, an introducing tube 29 also being slid on around the introducing means 33.

FIG. 4 shows, schematically, the elements which are to be slid onto the guide "J" 31, when the introducing ring 33 has been withdrawn. Inside the tubular sheath 39, there is thus found an intermediate catheter 41 in which there are lodged, concentrically, two fine guide tubes intended to facilitate the positioning of the prosthesis.

It should be noted that, in FIG. 4, the dimensions of the prosthesis have not been kept to, this prosthesis simply being shown schematically in its radially narrowed stare, ready to be implanted. With respect to the tubes 43, 45, it should be noted that the inner tube 45 is longer than the tube 43 and has a diameter $d_4$ and a length such that the distal terminal part 45a thereof passes through the hollow interior of the prosthesis 1, to end at 45'a, substantially in the vicinity of the distal end 39a of the sheath 39 in the immediate vicinity of which the distal end part 41a of the catheter 41, at the location of which the prosthesis has been propositioned, is likewise disposed.

The implantation procedure may be as follows:

Let it be supposed that an implantation using the percutaneous route and femoral approach via the right iliac artery 51 has been used.

When an access route has been provided through the skin at 47 (see FIG. 5), the guide thread 31 is slid via this path into the aorta, in such a manner that the distal end thereof is located slightly beyond the distal end 49a of the aortic aneurysm 49. The introducing means 33 and the tube 39 are then slid onto the guide thread from outside the body of the patient.

Once this tube has been introduced until it reaches the vicinity of the distal end of the guide thread, the assembly formed by the catheter 41 containing the prosthesis 1 and the two tubes 43, 45 is pushed into the interior of the sheath 39, until the prosthesis comes into the proximity of the distal end of this sheath, as shown in FIG. 5. The prosthesis 1 is then released into the aorta by drawing the sheath 39 and the catheter 41 towards the rear while the prosthesis is held back. It opens out radially until it is located as shown in FIG. 6, with its hooks 23 secured beyond the distal end 49a of the aneurysm and its legs 5, 7 directed towards the iliac arteries 51, 53. It should be noted, in FIG. 6, that the prosthesis 1 has been implanted at a fairly clear distance from the branching zone 54 of the primary iliac arteries, in such a manner that the two branches 5, 7 are, like the section 3, situated sufficiently far into the "principal" vascular duct (in this case the aorta 55).

To position the prosthesis 10, the sheath 39 may be left in position slightly lower in the aorta, the guide thread 31 itself preferably being kept in the same place.

A second intermediate catheter in the distal part of which the prosthesis 10 has been prepositioned, and where two guide tubes, identical to those 43, 45 which have already been discussed, have likewise been disposed, is then introduced through this repositioned sheath. It should be noted that the presence of the distal part 45a of the inner tube 45 in the vicinity of the distal end of the catheter 41 facilitates the engagement of this assembly on the proximal end 31a of the guide tube 31. Guided by this guide thread, which thus (in the example used) passes through the branch 5 of the prosthesis 1, it will be possible for the above-mentioned assembly to be slid into the interior of this branch (the diameters being adapted therefor). By means of a novel backward movement of the tube 39 and, above all, of the intermediate catheter, combined with holding back by the tube 43, the distal end 10a of the prosthesis 10 is positioned close to the leg 5 and, as in the present example, in the interior of one part of the leg 5 where it opens radially, until the framework 29 comes to bear on that of the prosthesis 1, in the stent zone 11b thereof.

When the various introducing tubes are withdrawn along the guide thread, the prosthesis 10 unfolds progressively until it reaches the interior of the right iliac artery 51, such that the part 27a thereof which is formed solely by the sleeve 27 is situated inside the overlap of the iliac aneurysm designated 56 in FIG. 6.

Attention is drawn to the fact that an overlap of the aneurysm of this type is in fact a contraindication for treatment by endoluminal positioning of a vascular prosthesis or vascular prostheses. Thus, the novel approach of the invention, which combines a treatment of this type with a relatively minor surgical intervention, such as, in this case, a surgical operation on the primary iliac bifurcation via a limited first iliac access route, permits a much less onerous form of surgery to be used than is the case with a treatment consisting entirely of surgery, and thus permits patients to be treated in better conditions.

Once the "prosthetic branch" 10 is disposed as shown in FIG. 6, the surgical intervention proper may commence. For this, the surgeon cuts into the iliac channel of the patient, in the subperitoneal area, as shown schematically at 57 in FIG. 7.

After having locally exposed at 99 the vessels 51, 51a, 51b and the aneurism 56 (which extends at least to the artery 51) and having pinched or clamped the regions which require it (especially by way of the loop 101 and the forceps 103 which make it possible to close temporarily to the blood flow the iliac 51 and the prosthetic branch 27 in its part 27a), the surgeon sections at 100 (FIG. 8) the appropriate vascular region, downstream of the aneurism in relation to the blood flow (in this instance the iliac vessel 51, towards its branching in the direction of 51a and 51b). If need be, he even cuts the "sick" section of 51.

Through the exposed region 99, the surgeon recovers the anastomosable prosthetic branch 27a which passes through the upstream cut vascular section 51. The embossing of the prosthetic branch allows a certain adaptation in length (see FIG. 10 where forceps 101' replace the loop 101).

Figure 9:
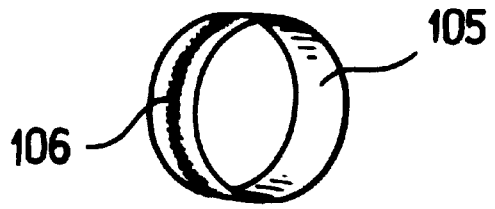
FIG. 9 shows in perspective a ring that can be used as antihaemorrhagic means between the sectioned upstream vessel and the anastomosable branch of the implant.
Figure 10:
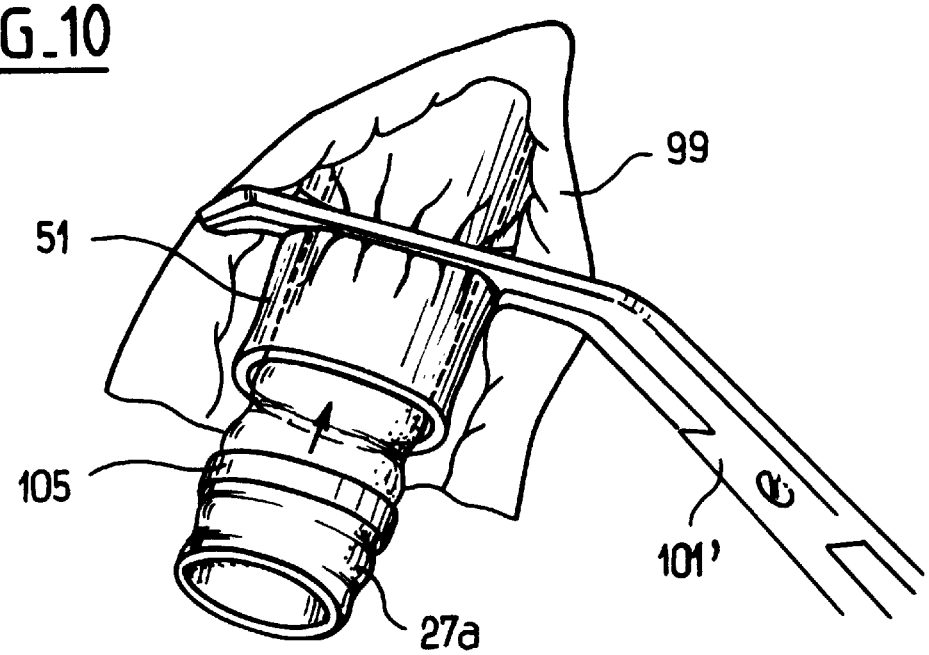
FIGS. 10 and 11 show the placing of this ring in position, at the site which has been exposed.
Figure 11:
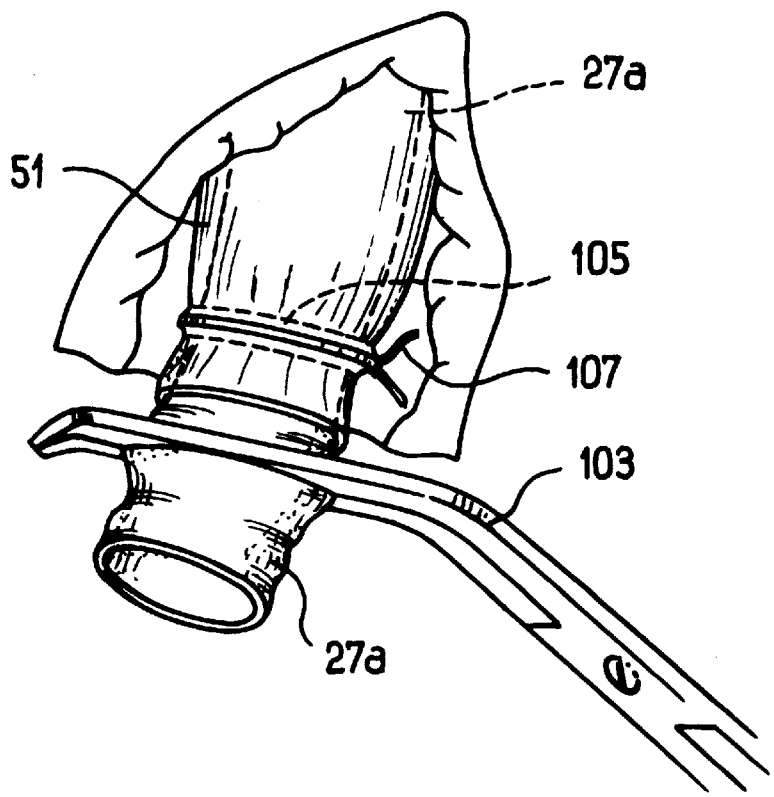
Figure 12:
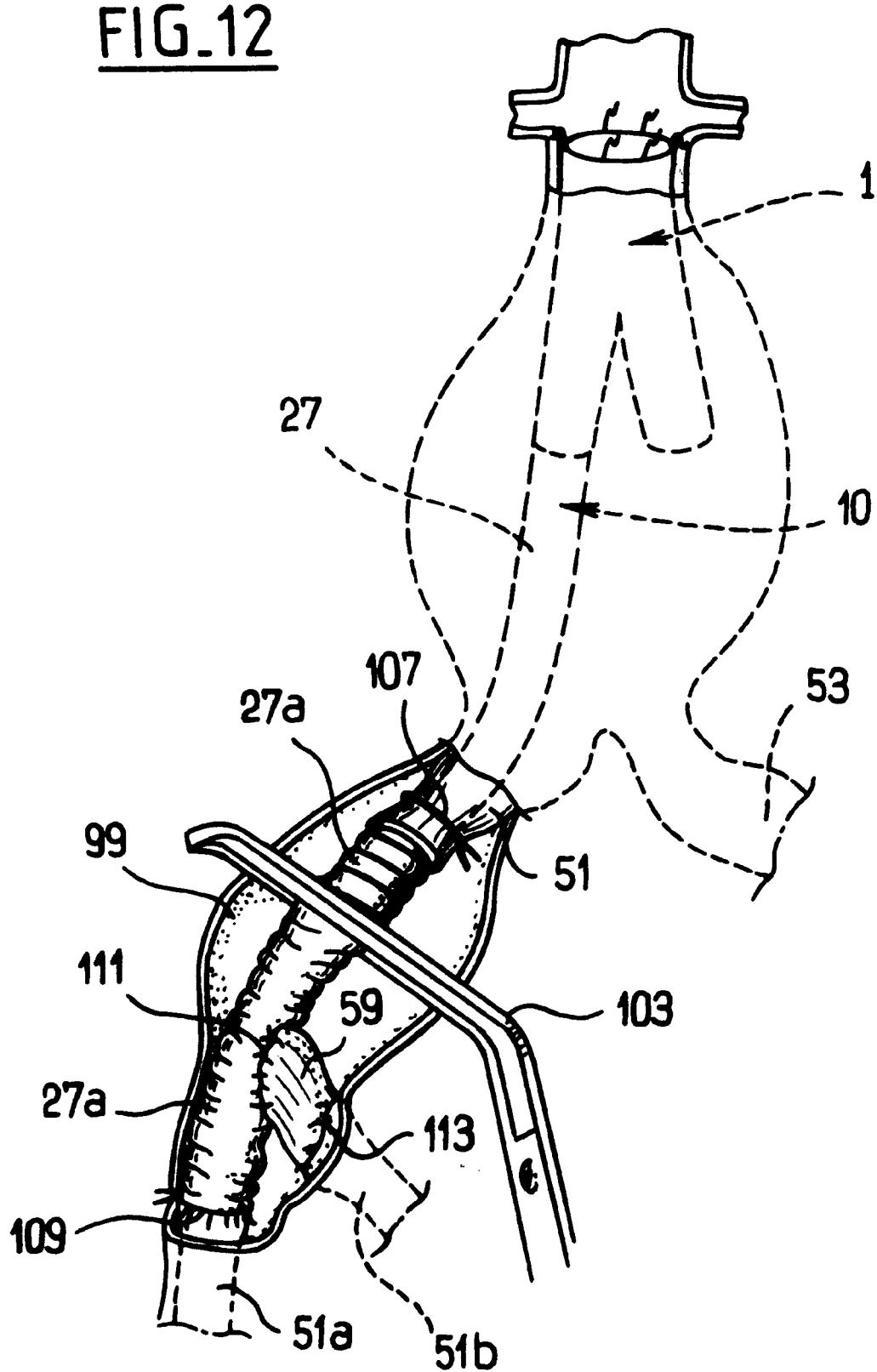
FIG. 12 shows the sutures between the said anastomosable branch of the implant and the downstream vascular region(s)
Figure 16:
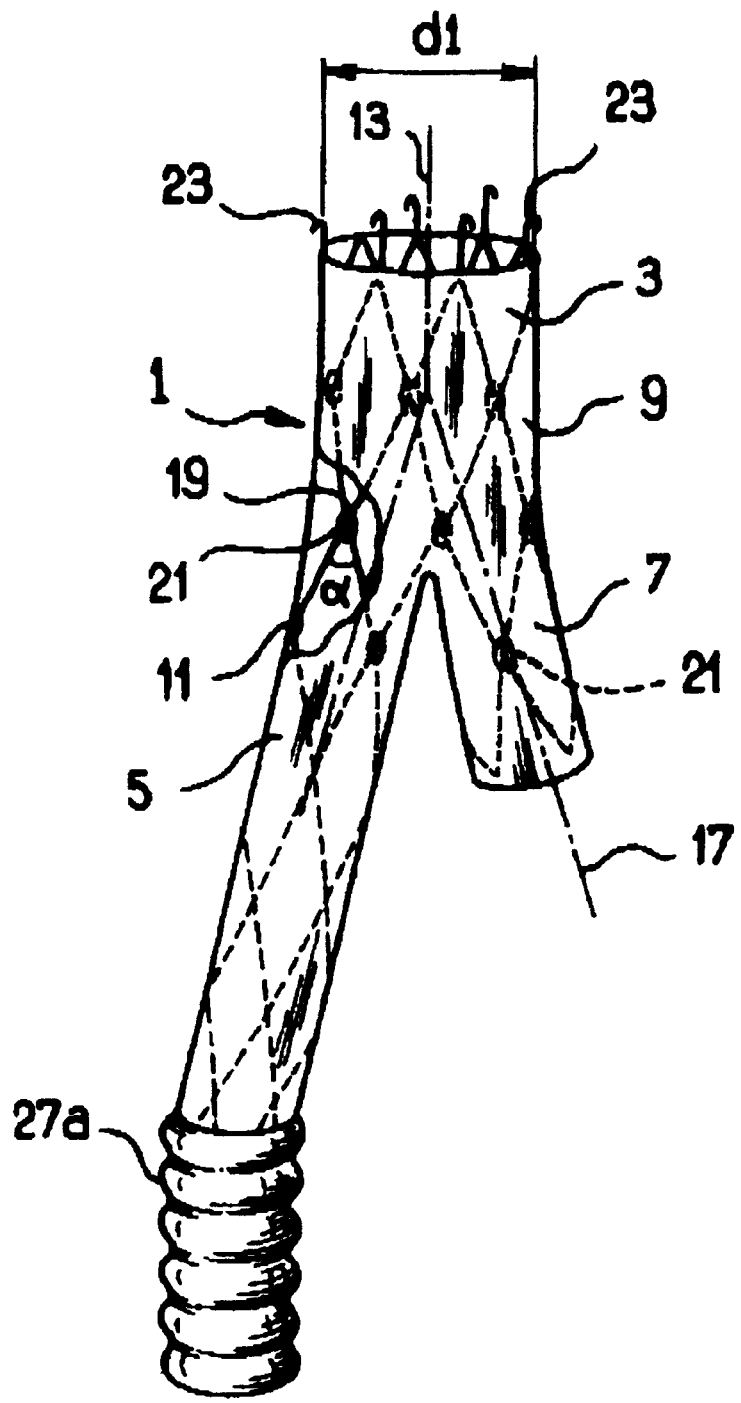
FIG. 16 is a perspective view showing a further embodiment of the present invention.

Then (see FIG. 10), the surgeon passes round the branch 27a (which re-emerges) the support ring 105 in FIG. 9, which has a resistance to compression. It may be a continuous ring (not split) made of metal (stainless steel) or of biocompatible plastic capable of clamping or fitting closely round the branch 27a, with, for example, a complementary internal shape (at 106) of at least one embossing fold of this branch in order to favour relative leaktight sealing.

Round the ring 105 (correctly positioned by sliding), the surgeon then places the upstream cut vascular section 51 (FIG. 11) which he clamps on it by means of the tie 107 without crushing the branch 27a, owing to the support means 105.

He may then, if need be, loosen the loop 101 (or the forceps 101'), a haemorrhage no longer being possible by leakage, round the branch 27a, of blood coming from upstream. The forceps 103 is kept in position.

The surgeon then connects (FIG. 12) to the downstream sectioned vascular section 51a the free end of the said portion 27a, by anastomosis (sutures 109), in such a way as to ensure appropriate revascularisation. The hypogastric artery 51b can then be reimplanted, with a lateral suture then, either directly on the prosthesis 27a or indirectly by means of a vessel substitute 59 itself anastomosed at each end (identification symbols 111 and 113).

Once the leaktight seal is ensured between the prosthetic branch 27a and the downstream vascular region(s) 51a (and 51b), the practitioner withdraws the forceps 103, thus allowing the blood to pass freely from the aorta, on the one hand into the outer iliac 51a, through the inside of the implant 1, 10, and on the other hand into the hypogastric artery 51b, through the lateral substitution section 59, itself anastomosed at its downstream end to the hypogastric artery.

A further "conventional" extension prosthesis (corresponding, if necessary, to the prosthesis 10), may then, by means of a second access route produced to provide access to the left iliac artery 53, be introduced, in a desired vicinity, via the percutaneous route, until it reaches the interior of the second branch 7 of the bifurcated prosthesis, in such a manner as to revascularise the artery 53 correctly (the implantation is not shown).

It should be noted that, by way of a variant of the embodiment, the prostheses in FIGS. 1 and 2 may be formed of a single assembly, one of the legs (5 or 7) or even the section 3 of the bifurcated prosthesis 1 thus having a length which is much greater than that of the other(s) and thus being terminated, in the distal part thereof, by the tubular sleeve 27a without the framework.

It should likewise be noted that, if necessary, the prosthesis 10 may even be used by itself (non-branched implantation zone).

Whichever is the case, once the above-mentioned operations have been performed, the assembly for implanting the prosthesis or prostheses is withdrawn from the body of the patient and the intraluminal and surgical access routes which have been formed are closed.

If interest is now taken in FIG. 13, the anatomical implant illustrated has been given the reference 60.

As in FIG. 2, this is an implant which, at least in its radially opened out state in the illustration, is in the form of a single tube of substantially circular section.

Over its length $L_3$, along its longitudinal axis 61, the diameter may be constant or otherwise.

Differing from the implant in FIG. 2, that in FIG. 13 has an anastomosable section of sleeve 63 having a length $L_4$ equal to more than half of the length $L_3$ and, as in this instance, equal to approximately ⅘ths of that length.

Over this length, the structure of the distal terminal portion of sleeve 63 has intrinsically a certain strength and may in particular naturally assume, by itself, the desired tubular shape, without requiring additional means. On the other hand, the proximal end portion 65 (length $L_5$) exhibits the open tubular form of FIG. 13 only under the effect of its supporting armature or stent 67 which is here in its radially opened out state and which, in the manner of the stents or armatures already disclosed in the prior art, supports the sleeve 65 which is fixed to it by any appropriate means, such as a suture thread, rings, eyelets, clips, etc.

The structure of the sleeve section 65 will very advantageously be that of a prosthesis sleeve for aneurism for percutaneous endoluminal implantation, that is to say, a non-self-supporting structure, of suitable biocompatible material such as polytetrafluorethylene (PTFE), "Dacron", polyethylene terephthalate (PET), or even "Mylar", cellulose acetate, or woven or knitted material, etc.

Typically, these materials are not worked to provide a self-supporting capability.

It is conventionally a question of a radially extensible texture (resiliently extensible or not) to follow the variation in diameter of the armature. Another solution may be a filament which is non-extensible, but produced with a deformable mesh which widens out when the implant is opened out.

It may even be a structure which is intrinsically imperfectly impermeable to blood (except for subsequent treatment).

On the other hand, the structure of the portion 63 is substantially self-supporting, in the manner of the bridging sheaths in vascular surgery.

It may there, in particular, be a structure having an elasticity, or at least a considerable axial deformation capacity, impermeability to blood, and on the other hand little or no radial deformability.

Dacron, PTFE or equivalent may be used. An embodiment in knitted or woven polyester as in U.S. Pat. No. 3,986,828, with a very low porosity, may also be envisaged.

For the axial deformability, the anastomosable section 63 may be embossed, as illustrated by the embossing folds 69 in FIGS. 13 and 14 (folds also visible in FIG. 2).

Thus, on an implant according to the invention, the section of sleeve (27, 65) supported by its armature or stent may have a first texture or structure adapted to the presence of the armature providing its mechanical strength and allowing it to open out radially once it has emerged from the implantation catheter, the complementary anastomosable portion of the sleeve being able, on the other hand, to be optimised in order to facilitate surgical recovery once the prothesis is implanted, and being therefore for this purpose particularly suitable to be sutured, while being intrinsically substantially impermeable to blood, naturally opened radially to permit automatically the internal circulation of fluid (circular section in particular) and offering more resistance to radial deformation than the other portion, (this second position being moreover advantageously not radially extensible).

As FIG. 15 shows, the "intrinsic" thickness $e_1$ of the portions 63, 65 may be identical. The total thickness $e_2$ of 63 may be greater, however, owing to the embossing. The thickness $e_1$ will be, for example, approximately 0.15 mm to 0.5 mm. The thickness $e_2$ may amount to approximately 0.5 mm to 1 mm.

As already indicated, the sections 63 and 65 may not only be intrinsically of different structure, but may also be produced in two separate parts connected to each other by any suitable means, such as a suture thread, clips, eyelets, etc., substantially coaxially and edge to edge, or even with a slight overlap, favouring relative leaktightness between the two sections with respect to the body fluid which is to circulate therein.

In FIG. 13 it will also be observed that the armature 67 is in the form of a tubular ring constituted by a metal wire (or a plurality of wires end to end) formed into zigzags or meanders closed on themselves and thus wound on a single stage or a single turn 31, having the particularity that the anastomosable section 63 and the armature 67 do not or practically do not overlap each other, such that the armature may take its full effect with respect to the "non-self-supporting" sleeve section 65, in particular at the moment where it is to be opened out radially in order to be applied tightly against the wall of the carrier duct.

All the observations which have just been made with regard to FIG. 13 apply also to the implant 70 in the shape of an inverted "Y" of FIG. 14, which can of course be implanted by the percutaneous endoluminal route.

In addition to the foregoing, this implant that can be inserted into a vessel comprises a short limb 71 and a long limb 73 which are produced from an anastomosable material, in the present instance embossed, this "Y"-shaped sleeve going up onto the main section 75 of the implant, to beyond the branching 77, over approximately ⅚ths of the length $L_6$ of the sleeve as a whole.

In the top part of the principal section 75, there is to be found again a radially deformable sleeve texture, at 79, the mechanical strength of which is provided by an internal stent 81 fixed to this section.

In this instance, the stent is a "lattice" stent of expanded metal, for example made of memory wire, such as "Nitinol" (registered trademark).

The stent passes from a constricted diameter, suitable for the implantation of the prosthesis by the endoluminal percutaneous route, to a widened diameter in a state implanted inside the receiving duct, under the action of an inflatable balloon round which the prosthesis will be mounted in its introduction equipment, in the manner of that which is described for example in EP-A-684 022.

In FIG. 13, as in FIG. 14, means for fixing the proximal end "with stent" of the prosthesis, such as hooks 83, are provided.

The rest of the implant (63 or 71, 73, 75) is on the other hand devoid of fastening means and stent, since this portion is intended to be anastomosed at, or towards, its free end, such as 63a, 71a or 73a (which is also the distal free end of the prosthesis or of the limb in question).

In the foregoing, it has been stated that the "anastomosable" portion (27a, 63, 71, 73) of the implant is devoid of supporting stent. This does not prevent the use of an anastomosable sleeve (made of PTFE for example) provided with a spiral (which can also be of the same material) or more generally with a radially resistant structure, favouring resistance to creasing and able to provide a slight longitudinal elasticity (possibility therefore of using a non-embossed sleeve). Such a "radially resistant" structure, however that may be, does not have the function of a "stent".

We claim:

1. Vascular prosthesis (10, 60, 70) arranged to be implanted by the percutaneous endoluminal route, comprising a flexible sleeve (27, 65, 79) to channel blood therein, and a tubular armature (or stent) (29, 67, 81) to which the sleeve is connected essentially coaxially, the armature being capable of having a first diameter or a second diameter larger than the first, so that the prosthesis is in the form of a single tube (10, 60) or bifurcated tube (1, 70) assuming a radially constricted state for its percutaneous vascular implantation, or a radially opened out state, once it is vascularly implanted, characterized in that it additionally comprises a vascularly anastomosable terminal portion of sleeve (27a, 63, 71, 73) which extends, or is added onto, the said flexible sleeve, beyond the armature, this portion configured to be anastomosed, in particular by suture, to at least one vessel or vessel substitute.

2. Vascular prosthesis for aneurism, that can be implanted by the percutaneous endoluminal route, comprising a flexible sleeve (27, 65, 79) and at least one tubular structure (29, 67, 81) forming an essentially coaxial stent or armature for the sleeve, in order to define a single or bifurcated tube, the said stent or armature assuming a first, constricted diameter for implantation by the percutaneous endoluminal route, by means of appropriate implantation equipment (33, 39, 41, 43, 45), or a second diameter larger than the first, when the prosthesis is already vascularly implanted, the prosthesis configured to be used as a prosthesis for the treatment of the spread of the said aneurism over a plurality of vessels (55, 51, 51a, 51b; 53), by vascular surgery, with anastomosis, of a vascularly anastomosable terminal portion of sleeve (27a, 63, 71, 73) extending, or added onto, the said flexible sleeve (27, 65, 79) with vessels or vessel substitutes.

3. Prosthesis according to claim 1, characterized in that it is configured to be used as a prosthesis for revascularisation in the case of a primitive iliac aneurism spreading over the hypogastric and outer iliac arteries.

4. Prosthesis according to claim 1, characterized in that the prosthesis is a bifurcated prosthesis (70) for treatment of an aneurism, comprising a principal tubular section (75) connected to secondary tubular sections (71, 73) one of which ends at its free end in the said vascularly anastomosable terminal portion of sleeve.

5. Prosthesis according to claim 4, characterized in that the free end of the principal tubular section (79) is provided with vascular fixing hooks (23, 83), while the free end of the secondary tubular sections (71, 73) is devoid of them.

6. Vascular prosthesis according to claim 1, characterized in that:

the part of the sleeve located essentially facing the armature (29, 67, 81) is radially extensible and/or assumes its radially open tubular form only under the action of the said armature which supports it, and then exhibits its second diameter, the anastomosable terminal portion of sleeve (27a, 63, 71, 75) is less radially extensible than the other portion (27, 65, 79, 27) and/or naturally assumes by itself a radially open tubular form.

7. Prosthesis according to claim 6, characterized in that the constituent materials or textures and/or the thicknesses ($e_1$, $e_2$) of the said sleeve parts, respectively facing the armature and anastomosable, are different.

8. Vascular prosthesis according to claim 6, characterized in that the anastomosable sleeve section (63, 71, 73, 75) has a capacity for deformation along the axis of the tube.

9. Prosthesis according to claim 6, characterized in that the anastomosable sleeve section does not extend, or practically does not extend, facing the armature (67, 81, 11, 29).

10. Prosthesis according to claim 1, characterized in that the anastomosable sleeve section (63; 71, 73, 75) extends over at least the greater part of the total length ($L_3$, $L_6$ of the sleeve.

11. Prosthesis according to claim 1, characterized in that it additionally comprises:

an annular support means (105) configured to be arranged around the anastomosable terminal portion of sleeve (27a; 63, 71, 73, 75) in order to obtain a leaktight seal with respect to the blood between the said annular means and the terminal portion, and a leaktight fixing means (107) in order thus to fix, round the support means, the cut vessel section (51) through which the anastomosable terminal portion is passed.

12. Assembly comprising:

the vascular prosthesis to be anastomosed, according to claim 1, and equipment (33, 39, 41, 43, 45) for endoluminal implantation of the said prosthesis by the percutaneous route, suitable for enclosing the prosthesis when its armature or stent exhibits its first, constricted diameter, for the purpose of its percutaneous implantation, the equipment comprising for that a sheath (39, 41) to introduce vascularly the prosthesis thus enclosed, and also an inner tube (43) configured to be inserted into the said sheath in order to play out the prosthesis vascularly from the said equipment, at the end of implantation.

13. Assembly comprising:

the vascular prosthesis to be anastomosed according to claim 1, which is in the form of a single, non-bifurcated tube (10), another vascular prosthesis (1) for treatment of an aneurism, configured to be implanted vascularly by the percutaneous endoluminal route, and being in the form of a bifurcated tube, and equipment for implantation of the said prostheses (1, 10, 60, 70) by the percutaneous endoluminal route.

14. Assembly comprising:

as the first prosthesis, the vascular prosthesis according to claim 1, and a second vascular prosthesis (1) for treatment of an aneurism, the second prosthesis, which is in the form of a bifurcated tube, itself comprising a sleeve (9) for channelling the blood and at least one tubular stent or armature (11) for its sleeve, the stent or armature being present (at 11a; 11b, 11c) at least at the two axial ends of the prosthesis (1) and having a first diameter or a second diameter larger than the first, in such a way that the second prosthesis is arranged to be implanted by the endoluminal percutaneous route, the said two prostheses (1, 10; 60, 70) configured to be arranged for connection between the said bifurcated second vascular prosthesis (1, 70) and the opposite end of the said first prosthesis from that provided with the said terminal section to be anastomosed.

15. Assembly according to claim 14, characterized in that the said first and second prostheses are configured to be connected to each other by engagement with support of the armature or stent (29) of the first prosthesis inside the armature or stent (11) in question of the second prosthesis (1).

16. An endoluminal vascular stent graft adapted to be implanted in a vascular zone of a human or animal body, the stent graft comprising:

a tubular flexible sleeve for circulating blood therein, and at least one radially expandable tubular framework bound to the flexible sleeve and having a distal end, the framework being adapted to have a first diameter when in a radially restricted state for implanting the stent graft, and a second diameter, larger than the first diameter when the stent graft is implanted, the flexible sleeve comprising a first portion and an extension, the extension extending beyond the distal end on the tubular framework, and having a free end that is unsupported by said tubular framework, wherein, said extension extends sufficiently beyond the distal end on the framework to permit manipulation of the extension such that it can be chirurgically anastomosed to a wall of the vascular zone and/or a vessel substitute, by means of connecting means passing through said extension and the wall of said vascular zone and/or said vessel substitute, and wherein the first portion of the sleeve is made of a first material and the extension is made of a second material.

17. An endoluminal vascular stent graft adapted to be implanted in a vascular zone of a human or animal body, the stent graft comprising:

a tubular flexible sleeve for circulating blood therein, and at least one radially expandable tubular framework bound to the flexible sleeve and having a distal end, the framework being adapted to have a first diameter when in a radially restricted state for implanting the stent graft, and a second diameter, larger than the first diameter when the stent graft is implanted, the flexible sleeve comprising an extension extending beyond the distal end on the tubular framework, said extension having a free end that is unsupported by said tubular framework and said extension extending sufficiently beyond the distal end on the framework to permit manipulation of the extension such that it can be chirurgically anastomosed to a wall of the vascular zone and/or a vessel substitute, after the tubular framework is radially expanded, by means of connecting means passing through said extension and the wall of said vascular zone and/or said vessel substitute, an annular support means adapted to engage the sleeve extension close to the free end thereof, inside the vascular zone in which said sleeve extension is disposed, and a leaktight fixing means for clamping the vascular zone around the annular support means without substantially crushing the sleeve extension.

18. An endoluminal vascular assembly adapted to allow a control circulation of blood in a blood vessel and configured especially for treating an aneurism, the vascular assembly comprising:

1) a first branching expandable tubular stent graft comprising:
   a) a branching tubular flexible sleeve having a main portion and first and second branching portions, each portion having a free end, the first branching portion being shorter than the second branching portion, and
   b) at least one expandable, tubular stent bound to the flexible sleeve, said at least one stent extending at the free ends of the main portion and of the first branching portion of the flexible sleeve, respectively,
   wherein the second branching portion has a terminal length at the free end thereof, said free end and said terminal length of the second branching portion being unsupported by said at least one stent, and the terminal length being sufficiently long to permit manipulation of said terminal length of the sleeve such that it can be chirurgically anastomosed to the vascular zone and/or a vessel substitute, by means of connecting means,
2) a second expandable tubular stent graft having a first free end and a second free end, and comprising:
   a) a tubular flexible sleeve adapted for circulating blood therein, and
   b) at least one tubular expandable stent bound to said flexible sleeve, said at least one tubular stent being adapted to have a first diameter when in a radially restricted state for implanting the second stent graft and a second diameter, larger and the first diameter, when the second stent graft is implanted,
   the flexible sleeve having a terminal length located at the first free end of the second stent graft, said terminal length and said free end that is unsupported by said at least one stent and said terminal length of the sleeve extending sufficiently beyond said at least one stent of the second stent graft to permit manipulation of the terminal length of the sleeve such that it can be chirurgically anastomosed to the vascular zone and/or a vessel substitute, by means of connecting means,
   the free end of the first branching portion of the first stent graft and a second free end of the second stent graft located opposite said first free end thereof being adapted to be mutually engaged for assembling the second stent graft to the first stent graft.

19. The prosthesis assembly according to claim 18, wherein the second stent graft further comprises fixing hooks disposed at the second free end thereof.

20. The prosthesis assembly according to claim 18 wherein the connecting means comprise a suturing means passing through the terminal length of the sleeve and a wall of the vascular zone and/or the vessel substitute.

21. The prosthesis assembly according to claim 18 wherein said at least one expandable tubular stent of the first branching expandable tubular stent graft is branched.

* * * * *